(12) United States Patent
Healy et al.

(10) Patent No.: US 6,692,532 B1
(45) Date of Patent: Feb. 17, 2004

(54) BONE REPAIR COMPOSITE MATERIAL

(75) Inventors: David Michael Healy, Ayr (GB); Thomas Gilchrist, Ayr (GB)

(73) Assignee: Fite Holdings Limited, Glasgow (GB)

( * ) Notice: Subject to any disclaimer, the term of this patent is extended or adjusted under 35 U.S.C. 154(b) by 0 days.

(21) Appl. No.: 09/787,384

(22) PCT Filed: Sep. 15, 1999

(86) PCT No.: PCT/GB99/03077

§ 371 (c)(1), (2), (4) Date: May 18, 2001

(87) PCT Pub. No.: WO00/16819

PCT Pub. Date: Mar. 30, 2000

(30) Foreign Application Priority Data

Sep. 19, 1998 (GB) ................................................ 9820369

(51) Int. Cl.⁷ ................................................. A61F 2/28
(52) U.S. Cl. ............................... 623/23.51; 623/23.56; 623/23.61; 623/23.63
(58) Field of Search ............................ 623/23.51, 23.61, 623/23.71, 23.73, 11.11, 16.11, 23.63, 23.56, 23.62, 17.11; 523/115, 116

(56) References Cited

U.S. PATENT DOCUMENTS

| | | | | |
|---|---|---|---|---|
| 4,239,113 A | * | 12/1980 | Gross et al. | 206/568 |
| 4,645,749 A | * | 2/1987 | Drake | 501/45 |
| 5,204,106 A | * | 4/1993 | Schepers et al. | 424/423 |
| 5,573,055 A | * | 11/1996 | Melling et al. | 164/15 |
| 5,707,962 A | * | 1/1998 | Chen et al. | 514/12 |
| 5,711,792 A | * | 1/1998 | Miller | 106/38.22 |
| 5,874,109 A | * | 2/1999 | Ducheyne et al. | 424/486 |
| 6,013,080 A | * | 1/2000 | Khalili | 606/86 |
| 6,019,765 A | * | 2/2000 | Thornhill et al. | 606/94 |
| 6,180,606 B1 | * | 1/2001 | Chen et al. | 514/12 |
| 6,309,420 B1 | * | 10/2001 | Preissman | 623/16.11 |
| 6,331,310 B1 | * | 12/2001 | Roser et al. | 424/423 |

FOREIGN PATENT DOCUMENTS

| | | | | |
|---|---|---|---|---|
| EP | 0 577 342 | | 1/1994 | |
| GB | 2099702 A | * | 12/1982 | A61F/1/00 |
| WO | WO 96/24364 | | 8/1996 | |

OTHER PUBLICATIONS

Brewster, N.T., et al. "Mechanical considerations in impaction bone grafting" *J. of Bone and Joint Surgery* 81–B:118–124 (1999).

Wheeler, K.E., et al. "Effect of bioactive glass particle size on osseous regeneration of cancellous defects" *J. of Biomed. Materials Research* 41:527–533 (1998).

Bergman, S., et al. "Bone In–Fill Of Non–Healing Calvarial Defects Using Particulate Bioglass® and Autogenous Bone" *Bioceramics* 17–21 (1995).

* cited by examiner

*Primary Examiner*—Bruce Snow
*Assistant Examiner*—Cheryl Miller
(74) *Attorney, Agent, or Firm*—Nixon Peabody LLP

(57) ABSTRACT

There is provided an admixture comprising morsellised bone particles and particles of water-soluble biodegradable glass. The particle size distribution and diameter range is preselected to produce an aggregate. Addition of the glass enables an admixture having aggregate characteristics and thus increased shear strength to be produced whilst simultaneously enabling bone regeneration to occur within the treated defect. The admixture is therefore useful in the repair of bone defects, especially primary joint arthroplasties, such as hip replacement operations.

23 Claims, 3 Drawing Sheets

BONE REPAIR COMPOSITE MATERIAL

SUMMARY OF THE INVENTION

The present invention relates to a composite material which is especially useful to repair bone in joints and other load bearing positions.

Operations to replace defective hip joints are now well-known and are performed routinely in the United Kingdom and western world and total hip arthroplasty (THA) is currently one of the most successful operations performed. The operation involves the removal of the patient's defective hip joint and its complete replacement with a prosthetic joint. The patient's quality of life is generally greatly improved throughout the time period that the prosthetic joint remains functional, and from the Swedish hip register the success rate at ten years post operatively lies at around 90%. Total knee arthroplasty is fast approaching similar levels of success. However, a major disadvantage of the prosthetic joint is its finite lifetime and the ultimate need for replacement of the prosthetic. The limitation on the lifetime of the prosthetic arises when the articulating surfaces become worn and debris from the worn prosthetic attracts a macrophage response. Chemicals released by the macrophages unfortunately tend to cause degradation of the bone around the prosthetic implant site, causing loosening of the prosthetic joint which can be difficult to combat. The success rate of subsequent revision hip surgery is significantly lower than for primary THA.

Various approaches have been made to overcome the bone defect around a hip joint. Examples include the use of a large custom-made prosthesis, but this is an expensive approach and has yielded poor results.

Autograft would provide the best bone for re-incorporation in impaction grafting, but donor site morbidity usually prevents harvesting autograft from an individual at the same time as performing their revision hip surgery. Femoral heads removed at the time of primary hip surgery are a ready, sterile supply of allograft, which is the next most preferable graft type. The immunogenic incompatibility between donor and recipient is not usually a problem and is further attenuated by the act of freezing. The increased demand and the move for centres to perform their own revision operations has prompted many smaller centres to set up facilities to perform their own bone banking of allograft femoral heads at the time of primary hip arthroplasty.

Cadaver allografts have also been used to pack the bone defect and ideally large amounts of bone could be harvested in a clean manner from cadaveric donors and then sterilised. However allografts carry a high risk of disease transmission (eg HIV and CJD) and those from cadavers often fail to incorporate into the host skeleton, proving to be of limited value. Nonetheless, utilisation of allograft bone is increasing as the number of revisions of failed joint arthroplasty rises and techniques for bone replacement gain wider acceptance. Future demands for allograft bone are expected to rise as the number of primary joint arthroplasties performed per annum increases and this will be further exacerbated as operations are offered to younger patients and the population as a whole, live longer. Current estimates place the total number of hip replacements performed world wide as over 800,000 per annum.

There is therefore a large and increasing demand for stores of bone graft.

BRIEF SUMMARY OF THE INVENTION

Bone graft alone, either morcellised or whole, has had some success in replacing lost bone stock. However, limited supply and increasing concerns regarding transmission of pathogens has prompted interest in synthetic materials. There has been an increasing interest in bone substitute materials, although their current use and future role have yet to be defined, together with cost-benefit analysis.

Inert materials with high mechanical strength have been tested clinically. Apatite-wollastonite (A-W) glass ceramic has been used in combination with milled allograft and fibrin glue with some success in revision THA's. Direct bonding between bone and A-W glass ceramic granules was seen histologically. There is however no replacement of the inert material with time to replace lost bonestock, should a subsequent revision be necessary. Interest in bio-active materials has evolved to address this problem. Osteogenic Protein-1 (BMP-7) (Stryker Biotech) is a growth factor in the TGF-$\beta$ superfamily and has been shown to stimulate bone producing cells in vitro and in vivo. It may also enhance bone incorporation around implants, whereas Hydroxyapatite (HA) may be an alternative to bone allograft. Pro-Osteon has been investigated as a bone void filler in several studies.

It is an object of the present invention to provide a material suitable for packing bone defects, for example in any fractured or broken bone, including facial bone, the jaw and teeth. The material is especially useful for packing bone defects in load bearing positions such as in primary joint arthroplasties (for example around prosthetic hip or knee joints) whilst simltaneously enabling bone regeneration to occur within the treated defect.

In one aspect, the present invention provides an admixture of biocompatible water-soluble glass (BWSG) particles and morsellised bone particles, wherein the particle size range and particle size distribution is pre-selected to be capable of forming an aggregate. The particle distribution may be selected according to the Fuller curve for maximal packing of particles.

Critically we have found that addition of BWSG, either as a bulking agent in a 50/50 mix by volume or by adding the particle size(s) needed to achieve the Fuller requirements, increases the shear strength of the bone. Desirably at least 10% by volume, more usually 25% or 40% by volume, of BWSG is present in the mixture.

As an example, the admixture may comprise particles of diameter 0.1 mm to 10 mm, preferably 0.2 mm to 8 mm, especially preferably 0.5 mm to 6 mm.

Where the diameters of the majority of the particles fall within the preferred range of 0.5 mm to 6 mm, the following typical particle distribution (which conforms to the Fuller curve) would produce a well-graded mixture:

particles 6.0 mm to 5.0 mm=7.0%
particles 5.0 mm to 4.0 mm=9.0%
particles 4.0 mm to 3.0 mm=11.5%
particles 3.0 mm to 2.5 mm=7.5%
particles 2.5 mm to 2.0 mm=9.0%
particles 2.0 mm to 1.5 mm=11.5%
particles 1.5 mm to 1.0 mm=16.5%
particles 1.0 mm to 0.5 mm=28.0%

The admixture of the present invention exhibits excellent mechanical stability and are able to "cement" the prosthesis into healthy bone tissue in a manner similar to a bridge pile sunk into a gravel aggregate.

Improved results have been obtained where the bone particles are washed before use. We believe that washing removes the "wet slurry" produced due to increased fat and marrow release in finely ground bone particles. The presence of "wet slurry" decreases the shear strength of the composite.

The critical properties of the aggregate formed by the admixture are particle size distribution, angle of internal friction, dilatancy and degree of fluid saturation. The fluid may be any sterile fluid (such as water or a protein solution) but advantageously may contain soluble growth factors able to promote bone repair and/or certain bone stem cells or tissue engineered bone forming cells.

To produce the strongest aggregate (or aggregate most resistant to shear stress), the material of the present invention should have the following characteristics;
1. "Ideal" particle size distribution;
2. Low state of Hydration;
3. Sequential layered impaction of well mixed material;
4. Impacted with a large amount of Joules/Volume; and
5. Rigidly contained (use of Meshes).

"Ideal" particle size distribution refers to a mixture of different particle sizes that produces the strongest aggregate. As explained above, this has been determined by Fuller who mathematically determined the graphical curve (Fuller Curve) of particle distribution that represents the sequence of spheres to fit the "gaps" which if carried to infinitely small sizes of spheres will allow a pyramid to be constructed. When considering irregularly shaped particles, where there is not an infinite supply of ever diminishing particle sizes, it is accepted practice to use a linear log of the range of available sizes, to determine an ideal mixture.

Experts in Soil Mechanics have found that the mechanical properties of any collection of particles, or "aggregate" is dependent upon the particle size distribution, and not on the individual properties of the particle. The particle size distribution of all test materials in this project was therefore determined using sieve analysis.

The Linear Log Line (rather than the Fuller Curve) has certain advantages in experimental use for two main reasons:
1. Fuller is based upon packing of "spheres", which is quite different from sharp or angular particles.
2. The Linear Log straight line is considered to represent "well graded" soils in civil engineering (i.e. that a large distribution of particle sizes is present). Well graded soil will attain larger densities on compaction than others and therefore will be more resistant to shear. As current bone mills produce a finite range of particle sizes (~5 mm to ~0.3 mm), drawing a straight line between the two sizes on the log plot is the best in a "soil mechanics" sense.

Also of note, is that in theory, Fuller requires almost 30% of its particle sizes below the minimum currently produced by bone mills. This means that by using Fuller's curve, there may even be loss of strength. Using a second mill to produce the very small particles may potentially block the interstices of the graft and interfere with the neovascularisation of impacted graft. Notwithstanding the above, a derived mixture (based on Fuller, mathematically determined as 34% 3 mm Aesculap mill+66% 6 mm Aesculap mill) was produced, compacted and shear tested.

Our studies have shown that:
1. Well-graded aggregates of saturated allograft bone/BWSG will not differ in stress/strain behaviour under compaction.
2. Well-graded aggregates of saturated allograft bone/BWSG will not differ in speed and quality of reincorporation in a sheep limb bone defect model.
3. Well-graded aggregates of saturated allograft bone/BWSG will not differ in reincorporation or in mechanical stability over a twelve month period in a sheep hip replacement model.

Preferably the water-soluble glass controllably releases calcium and/or phosphate moieties and dissolves steadily over a time period appropriate to bone repair. The inclusion of the glass is envisaged to promote healthy bone growth more effectively than achievable using only morsellised bone particles. In one embodiment other active ingredients—especially those able to combat infection or disease or to promote healthy bone growth—may be controllably released as the water-soluble glass dissolves. Particular mention may be made of growth factors active in bone tissue and of bone stem cells or tissue engineered bone forming cells.

In a further aspect, the present invention provides a method of repairing defective bone in a load-bearing position, said method comprising compacting an admixture as described above into the bone defect.

In one embodiment, the bone defect comprises the area around a prosthetic (especially a prosthetic hip joint) damaged by macrophage activity.

Phosphorous pentoxide ($P_2O_5$) is preferably used as the glass former of the biodegradable glass used in the admixture.

Generally the mole percentage of phosphorous pentoxide in the glass composition is less than 85%, preferably less than 60% and especially between 30–60%.

Alkali metal's, alkaline earth metals and lanthanoid oxides or carbonates are preferably used as glass modifiers.

Generally, the mole percentage of alkali metals, alkaline earth metals and lanthanoid oxides or carbonates is less than 60%, preferably between 40–60%.

Boron containing compounds (eg $B_2O_3$) are preferably used as glass additives.

Generally, the mole percentage of boron containing compounds is less than 15% or less, preferably less than 5%.

Other compounds may also be added to the glass to modify its properties, for example $SiO_2$, $Al_2O_3$, $SO_3$ sulphate ions ($SO_4^{2-}$) or transition metal compounds (eg. first row transition metal compounds).

Typically the soluble glasses used in this invention comprise phosphorus pentoxide ($P_2O_5$) as the principal glass-former, together with any one or more glass-modifying non-toxic materials such as sodium oxide ($Na_2O$), potassium oxide ($K_2O$), magnesium oxide (MgO), zinc oxide (ZnO) and calcium oxide (CaO). The rate at which the glass dissolves in fluids is determined by the glass composition, generally by the ratio of glass-modifier to glass-former and by the relative proportions of the glass-modifiers in the glass. By suitable adjustment of the glass composition, the dissolution rates in water at 38° C. ranging from substantially zero to 25 mg/cm$^2$/hour or more can be designed. However, the most desirable dissolution rate R of the glass is between 0.01 and 2.0 mg/cm$^2$/hour.

The water-soluble glass is preferably a phosphate glass, and preferably comprises a source of silver ions which may advantageously be introduced during manufacture as silver orthophosphate ($Ag_3PO_4$). The glass preferably enables controlled release of silver or other metal ions, for example Zn, Cu, Mg, Ce, Mn, Bi, Se and Cs (preferably Ag, Cu, Zn and Mg) and other constituents in the glass and the content of these additives can vary in accordance with conditions of use and desired rates of release, the content of silver generally being up to 5 mole %. While we are following convention in describing the composition of the glass in terms of the mole % of oxides, of halides and of sulphate ions, this is not intended to imply that such chemical species are present in the glass nor that they are used for the batch for the preparation of the glass.

The optimum rate of release of the metal ions (eg Ag, Cu, Zn or Mg, or any of the other metal ions mentioned above)

into an aqueous environment may be selected by circumstances and particularly by the specific function of the released metal ion. The invention provides a means of delivering metal ions to an aqueous medium at a rate which will maintain a concentration of metal ions in said aqueous medium of not less than 0.01 parts per million and not greater than 10 parts per million. In some cases, the required rate of release may be such that all of the metal added to the system is released in a short period of hours or days and in other applications it may be that the total metal be released slowly at a substantially uniform rate over a period extending to months or even years. In particular cases there may be additional requirements, for example it may be desirable that no residue remains after the source of the metal ions is exhausted or, in other cases, where the metal is made available it will be desirable that any materials, other than the metal itself, which are simultaneously released should be physiologically harmless. In yet other cases, it may be necessary to ensure that the pH of the resulting solution does not fall outside defined limits.

Generally, the mole percentage of these additives in the glass is less than 25%, preferably less than 10%.

In a preferred embodiment the BWSG comprises 20–35 mole % $Na_2O$; 18–30 mole % CaO and 45–60 mole % $P_2O_5$.

BRIEF DESCRIPTION OF THE DRAWINGS

The present invention will now be further described with reference to the following, non-limiting, examples and figures in which.

DETAILED DESCRIPTION OF THE INVENTION

EXAMPLE 1

Biomechanical Aspects—Shear Testing and In-vitro Modelling

Figure 1:
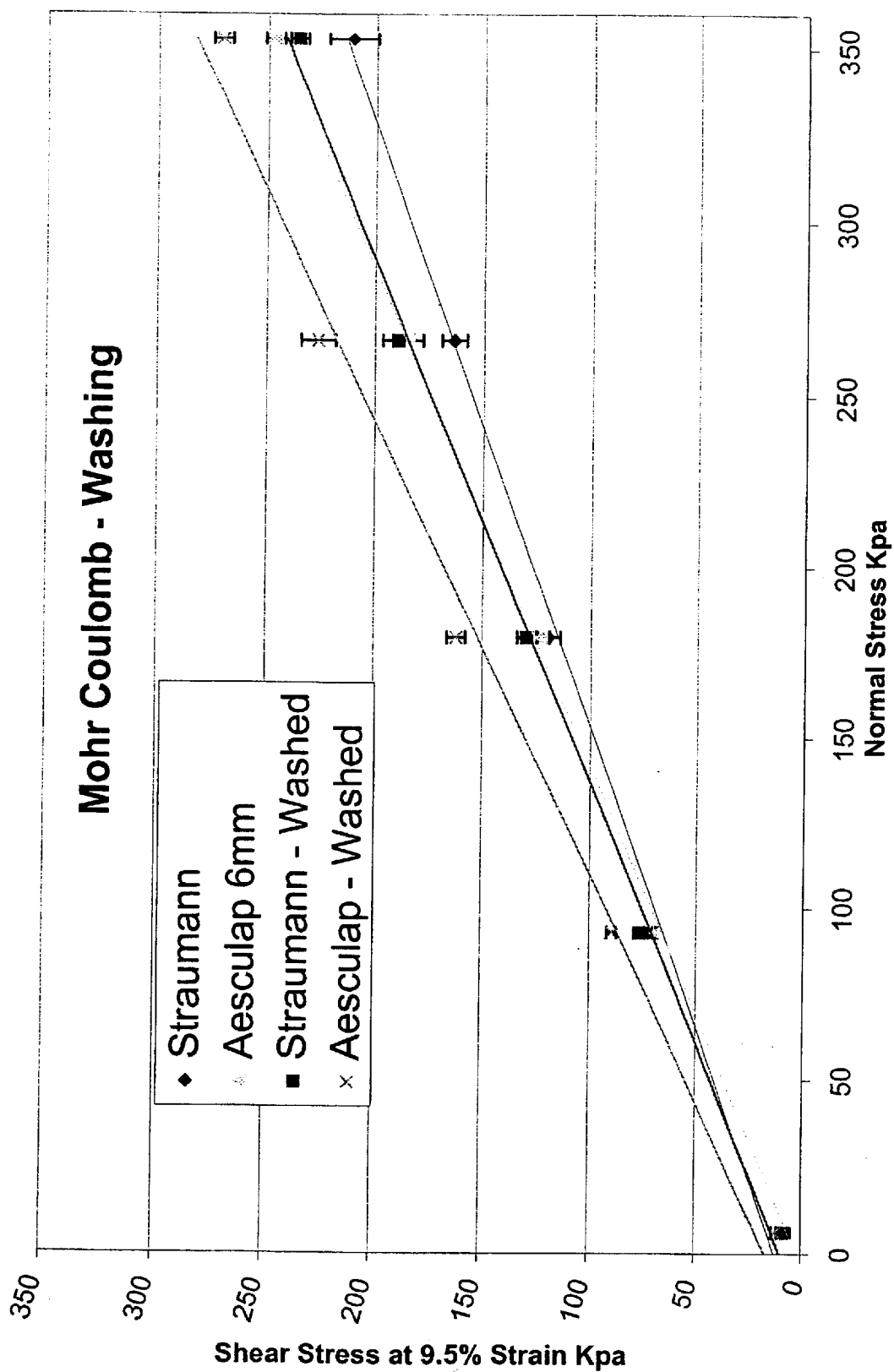
FIG. 1 is a graph showing the Mohr Coulomb values for 100% bone graft milled with a Straumann mill (Straumann), milled with a 6 mm Aesculap mill (Aesculap 6 mm), or the washed milled products of these mills (Straumann washed and Aesculap washed).

The tests in this example were performed using a large stock of fresh frozen human bone (femoral heads) obtained from a "bone bank", much like the clinical scenario. There were severe limits on availability of graft. The mechanical tests were limited to twenty-five for each test sample. Each test sample represented a random sample taken from the well-mixed combination of ten femoral heads that had been milled together. All tests needed to be performed with adherence to Health & Safety Guidelines using Universal Precautions.

The particle size distribution curves for each mill was determined by sieving graft produced from five femoral heads passed through each mill. Each different mechanical test required ten femoral heads, which were also prepared and milled in the same way. This involved, thawing in warm saline, removal of soft tissue and cystic areas, removal of all cortical bone remnants such as the femoral calcar and division into large chunks before milling. The femoral heads were taken at random from the store and the milled graft was thoroughly mixed in a single container to reduce the variation between different femoral heads.

For the mechanical tests, the mixture was then divided into five equal samples, which were each tested separately at the five different axial loads. Although more than five test samples would have been an advantage, it was not possible to divide the original sample into more than five groups and still have enough for each test. The results are presented as a "family of curves"—five individual lines at each of the five loads. All samples were kept at room temperature, in moisture retaining containers during the tests.

Materials and Methods

An Endocots™ Sieve shaker was used for all analyses. Bone graft that had been milled from currently used bone mills was sieved through a range of sieve sizes to determine the range. 99.99% of this bone was trapped and separated between the following sieve sizes; 5.6 mm, 4.0 mm, 2.8 mm, 2.0 mm, 1.4 mm, 1.0 mm, 0.71 mm, 0.5 mm and 0.3 mm. This range allowed determination of 8 fractionations less than 5.6 mm.

The wet spray head adapter, sealer rings and collection tub was used for the wet analyses. A spray head of water at 35–40° C., flowing at 10L/min was used to wash the bone across the sieves. Each sample was vibrated at 50 Hz with intermittent vertical oscillation (Level 9, 2 seconds off, 5 seconds on) for 90 minutes. The first most apparent finding with this regime was that there was a significant problem with sieving wet graft. During the wet sieving process it was noted that "clumping" of graft on the upper side of each sieve occurred. This was thought to be due to a combination of the natural hydrophillic nature of the graft and also the effect of small gelatinous strands of soft tissue, that were still present within the milled bone, preventing the normal passage of smaller particles to their correct sieve level. Increasing the fluid flow rate, oscillation power or time did not reduce this phenomenon. The wet bone from each sieve tray was weighted before and after being placed on a damp towel in an incubator at 40° C. and 40% humidity overnight. The incubator was utilised to remove the fluid used to wash the graft through the sieving tower, as this would necessarily have been included in the first measurement. It was found that the relative proportions of graft, when determined by weight, was not affected by the state of hydration. What was noted however was that the graft was no longer "clumping" after the period in the incubator, and the particles themselves were still "moist" and as flexible as when they were first milled. For this reason the samples were then re-sieved moist without washing and noted to pass rapidly to their correct sieve level. Each sample was vibrated at 50 Hz with intermittent vertical oscillation (Level 6, 5 seconds off, 2 seconds on) for 60 minutes. After this time, each sieve tray was weighed and sieving continued for a further 5 minutes until there was a less than 1% change in weight of any of the trays. The new particle size distribution was then determined.

Biocompatible Water-Soluble Glass

The BWSG used in all of the examples had the following composition:

33.4 mole % $Na_2O$ 19.6 mole % $CaO$ 47.0 mole % $P_2O_5$

Dissolution rates annealed=0.8189 $mg.cm^{-2}.hr^{-1}$.

(fused=1.0312 $mg.cm^{-2}.hr^{-1}$.) and the glass was used in annealed form.

Linear Log and Fuller Curve Graft Determinations

As the sieve sizes used were based on a logarithmic scale, if the same amount of material was used from each sieve, then an aggregate that had a linear log particle distribution could easily be created. The mechanical testing of a pure bone Linear Log could therefore not be performed on fresh milled graft as it necessitates sieving. Fresh graft was used to produce the best approximation to the Fuller curve, based on the mathematical calculation of the ideal proportions from the two mills either side of the curve. This technique, rather than adding different amounts of sieved graft to produce a Fuller Curve, was used as it is nearer to what may happen in the clinical setting.

Different mills have previously been shown to produce different particle size distributions when a small amount of preserved bone was analysed. These tests confirmed this early finding in fresh human bone graft. The distribution curves are similar in shape for both the 6 mm Aesculap mill and the Straumann mill. The Straumann mill produced a relatively well graded mixture of larger bone particles compared to the poorer graded, smaller Aesculap mill. This latter mill was nearer to the Linear Log line and Fuller curve and thus would be expected to have improved mechanical properties to resist shear. Interestingly sheep bone prepared in a similar manner has a different distribution curve (unpublished data), and may reflect the clinical impression of increased brittleness of ovine bone.

Shear Testing

Two basic elements are required to test the mechanical properties of an impacted aggregate such as bone graft. Firstly a device to simulate the act of impaction, ideally replicating the amount of energy applied during impaction grafting, and secondly a device that tests the shear strength of an aggregate. Basic engineering principles of Youngs Modulus or beam testing cannot apply due to the particulate nature of the test substance. Shear testing allows properties such as the angle of internal friction, cohesion and Mohr Coulomb failure envelopes to determine the various properties of aggregates.

Proctors Impactor Design

The impacted pellet produced by the impactor, to be tested in the shear tester, should ideally have a diameter at least twenty times the average particle size. Too large a diameter would waste test material, which was limited in its supply. As our particle range was from 300 microns to 5.6 mm, an impactor diameter of 60 mm was considered optimal. The design was modified to allow for the compaction of wet material such as fresh human graft. To allow moisture, but not particles to escape (as liquids are relatively incompressible), minute holes were LASER drilled into the piston head. Fluid was also able to escape between the impactor rings. The plunger was originally designed to rise and fall with each blow, which had a considerable damping effect, especially when wet. This was modified to allow an equivalent mass to fall, acting on the plunger without damping. The energy applied to each test pellet was equivalent to one "standard femoral impaction". This has previously been calculated by measuring the energy applied to a force plate by the distal end of a femur, undergoing a 'routine' impaction grafting.

Sequence of Impaction

Each material to be tested was introduced into the top of the impactor in three equal portions, to ensure even compaction.

The first third was placed evenly in the chamber, the piston lowered onto the sample and the weight dropped 24 times from the given height. The piston was then rotated (to prevent test material sticking to its underside) and removed.

The middle third of the test sample was then laid on top of the first and impacted 24 times as before.

The remaining third was then added and impacted in a similar fashion, so that the finished pellet received 72 blows.

The impaction rate was approximately 1.5 Hz, similar to the clinical scenario and slow enough to allow fluid to escape.

Cam Shear Tester Design

The Cam (Cambridge) Shear Tester was based on the original design by Jenike. The internal diameter of the test cell of the Cam shear tester was exactly the same as the Proctors impactor (60 mm)—and thus would accept the pellets produced from the impactor exactly, based upon the ideal of at least twenty times the diameter of the average test particle. The metal parts in the vicinity of the test material were fabricated in aluminium, brass and stainless steel to allow testing of "wet" material without corrosion. The test cell itself was not sealed and allowed for some escape of fluid on application of the axial load, similar to the clinical situation. A circular test cell was used to reduce "edge effect", which can be a problem with square test cells.

The lower shearing ring was fixed to the base plate the upper ring was mobile. A push rod attached to the upper ring received the shearing force during testing. This rod would cause the upper ring to move a constant distance in a constant time (constant strain rate) relative to the lower ring, and hence apply a shear stress to the cell contents. A load cell (force transducer) at the tip of the push rod recorded the load applied. The distance travelled was recorded with a linear voltage displacement transformer (LVDT) in mm.

Five separate axial loads were applied and tested independently for each sample. The axial weights were; 1.75 Kg (the weight of the hanger alone), 26.75 Kg, 51.75 Kg, 76.75 Kg and 101.75 Kg. These weights were chosen to produce a family of curves within the range of normal human mechanical loading of impacted graft in a revision hip replacement.

Sequence of Testing

The test sample was immediately placed within the shearing rings after it had been impacted, as above. The base of the impactor was removable and allowed docking with the upper shear ring. The piston was used to push the pellet into the test cell without disruption to its integrity. The impactor was then removed.

The brass axial load plate was placed over the test material to distribute the axial load evenly and contain the test sample within the test cell. The axial load hanger was then gently lowered onto the brass plate so that the load pin engaged with the recess. The test sample was then left to equilibrate for five minutes in the test cell. During this time the load cell was brought up to the push rod.

The test then commenced, with the volt meter readings for both the LVDT and load cell being recorded.

The test was deemed complete when the load cell detects an obvious failure (dramatic drop in current) or the load cell voltage remains constant for a long period.

The sample was removed, broken up and re-mixed, together with any lost fluid (collected with a fine brush) and re-impacted as above. The pellet was then tested as above but with an additional 25 Kg weight on the hanger.

The above sequence was repeated until a family of curves has been generated for the one sample up to 101.75 Kg's.

All equipment was then thoroughly cleaned and dried before the next test.

Validation

The Cam Shear Tester, the LVDT and load cells were calibrated with sands of known shear strengths.

Throughout the entire testing procedure all samples were kept moist in air-tight containers to prevent drying.

The following comparisons of materials were made:
a) The mechanical properties of fresh bone graft milled in two different bone mills (Aesculap 6 mm mill and Straumann mill) were compared.

Results

The Mohr Coulomb failure envelope was derived from the stress/strain curves.

There are large differences between the mechanical properties of fresh human bone graft derived from a 6 mm Aesculap bone mill compared to the Straumann mill. These two mills were chosen due their widely different particle size distributions. Theoretically it was hypothesised that the poor grading of particles produced by the Straumann mill would produce an aggregate less resistant to shear. This appears to be borne out in the shear tests (see FIG. 1).

Thus there is a large difference in the mechanical properties of fresh bone graft prepared in different mills.

b) "Idealised" bone graft was compared to the material of paragraph (a) above.
"Idealised" bone graft was prepared in two different ways:
  i) admixture of 33% 3 mm Aesculap and 66% 6 mm Aesculap milled bone (Aesculap Idealised), or
  ii) Sieve separated and reconstituted particles, following the Fuller curve requirements (Aesculap linear log (washed)).

Results

Figure 3:
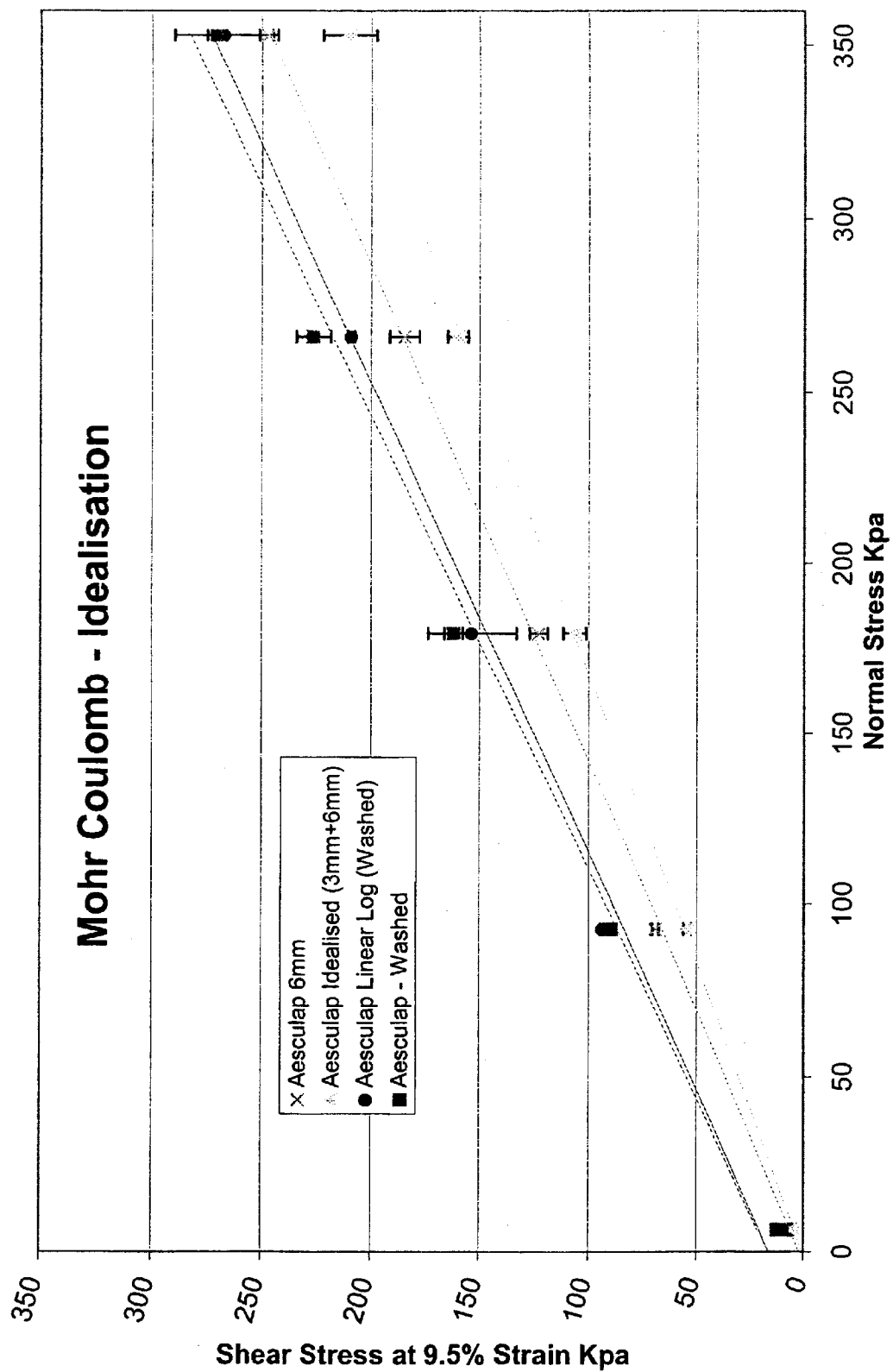
FIG. 3 is a graph showing the Mohr Coulomb values for 100% bone graft milled with a 6 mm Aesculap mill (Aesculap 6 mm), the washed milled products of this mill (Aesculap washed), a 33:66 (by volume) mixture of bone graft milled with Aesculap 3 mm and 6 mm mills (Aesculap Idealised) and Aeculap milled, sieve separated and reconstituted bone particles folowing Fuller curve requirements (Aesculap linear log).

The theoretical fresh mixture based on the Fuller curve was weaker than graft from the standard parent mill. This may be due to an effect from the 3 mm mill, possibly due to increased fat and marrow effect from the inherently smaller cancellous bone fragments. The theoretical washed, sieved and reconstituted mixture based on the Linear log line was stronger than fresh graft from the parent mill (see FIG. 3).

c) Idealised mixed graft prepared by milling bone graft with the Straumann mill and adding BWSG particles having the particle sizes to ensure the whole mixture accorded to Fuller characteristics.

The idealised mixed graft was compared to bone graft alone milled either in the Aesculap 6 mm mill or in the Straumann mill.

Results

There was a significant improvement in the ability of bone graft to resist shear after the addition of the missing particle sizes. This was seen in the Straumann mill on the addition of bioactive glass. It could be expected that such an improvement would be less marked on idealisation of the Aesculap mill, as it already has a relatively good grading. It is interesting to note that the cohesion of the Straumann mill is the same with or without bioactive glass, but the slope is steeper with the additive.

d) A 50/50 mixture by volume of bone graft milled by 6 mm Aesculap mill plus either idealised BWSG or TCP/HA. These two test mixtures were compared to the test mixture of paragraph c).

Results

Figure 2:
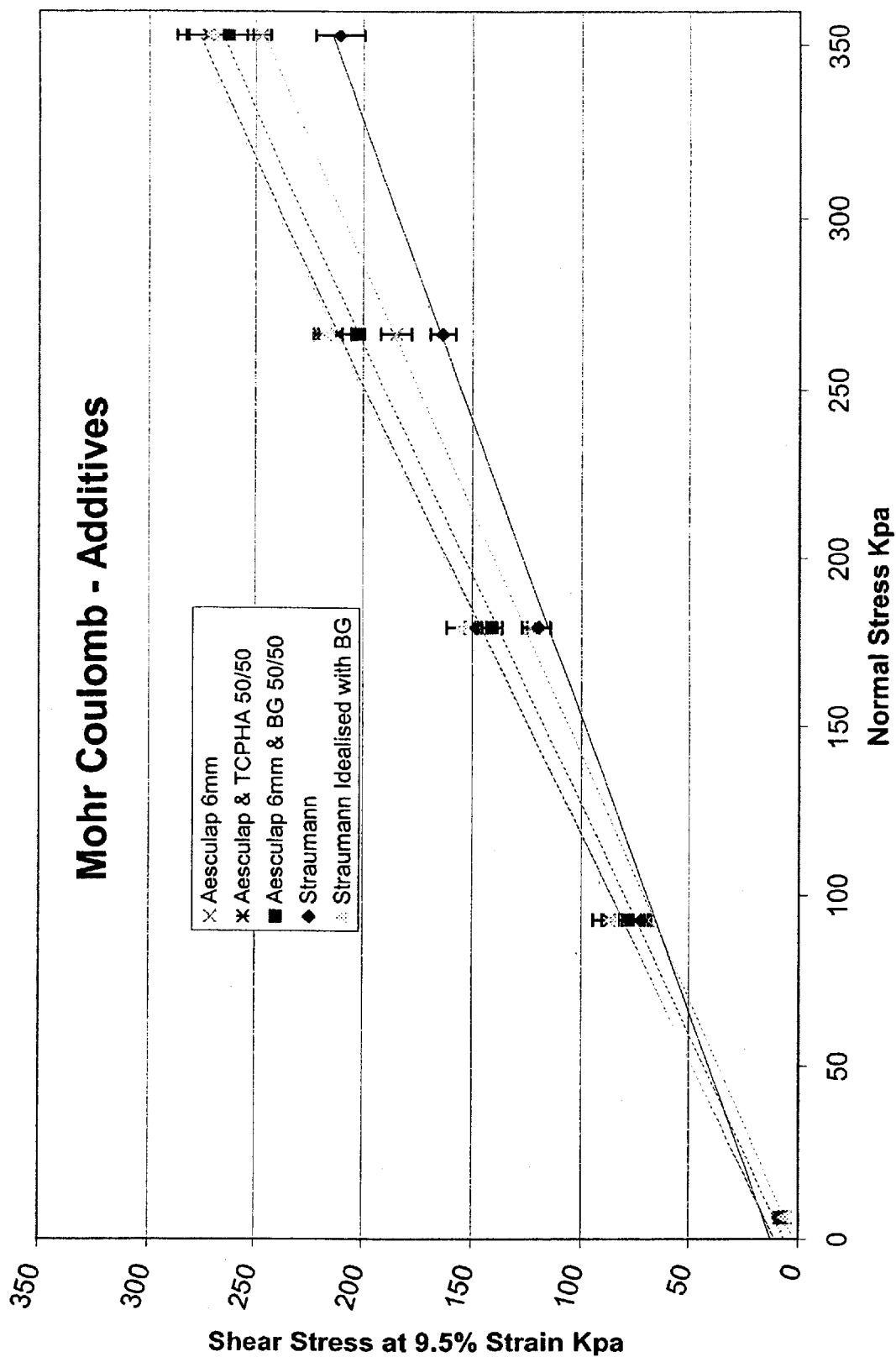
FIG. 2 is a graph showing the Mohr Coulomb values for 100% bone graft milled with a Straumann mill (Straumann), milled with a 6 mm Aesculap mill (Aesculap 6 mm), or admixtures formed from a 50:50 (by volume) mixture of triphosphate calcium hydroxyapatite (TCPHA) with the milled products of the Aesculap 6 mm mill (Aesculap & TCPHA) or of biocompatible water-soluble glass with the milled products of the Aesculap 6 mm mill (Aesculap & BG), or an admixture formed from the milled product of the Straumann mill together with biocompatible water-soluble glass particles of the size and quantity needed to form an "idealised" aggregate (Straumann idealised with BG).

All bone graft when combined with either bioactive glass or (tricalcium phosphate/hydroxyapatite) TCP/HA became more resistant to shear. This effect was seen in bone from both bone mills, and was particularly noticeable in the Straumann mill. This is possibly due to the greater overall improvement in the mixture grading when Straumann millings are combined with a well graded additive, compared to the Aesculap mill, whose initial grading is already good. The difference in the Mohr Coulomb slope between a 50/50 mixture of biocompatible water-soluble glass, compared to TCP/HA was minimal (see FIG. 2).

e) Washed milled graft (either 6 mm Aesculap milled particles, Straumann milled particles or 100% bone graft prepared by sieving and reconstituting the mixture so that particle size distribution accorded to the Fuller curve) were compared to the mixtures of paragraph a).

Results

It was seen with both mills that the simple act of washing markedly improves the ability of the aggregate to resist shear. In fact the inadequacies in grading that weaken the properties of bone from the Straumann mill can be removed by washing. However, washing of an already well graded mixture will further enhance the mechanical properties (see FIG. 1).

EXAMPLE 2

In Vivo Testing

Full mouth mature Grey Face ewes, weighing more than 60 kg, were used in this example. The sheep were purchased from a single breeder to ensure a uniform environmental and genetic background.

Preparation of Allograft Bone

Allograft sheep metaphyseal bone was obtained under sterile conditions following sacrifice of 2 sheep.

The proximal humerii, proximal femora and distal femora were removed under sterile conditions, cleaned of soft tissue and cut from their diaphyses to produce 500 g of cancellous graft. These were then divided into two equal groups and passed through a small (3 mm diameter) and large (6 mm diameter) bone mill respectively. One third of the graft from the large mill was mixed with all the graft from the small mill to produce a more uniform particle size distribution which represents an 'idealised' mixture.

Four test mixtures were produced, as follows:

Large mill graft idealised with bioactive glass; Idealised bone graft with idealised BWSG (as used in Example 1) in a 50/50 by volume mixture; Idealised bone graft alone; Idealised BWSG (as used in Example 1) alone.

Group 1 was produced by previously determining the particle size distribution of sheep bone produced from the large mill, then adding the correct amount by volume of bioactive glass of each particle size to produce a linear log particle size distribution. Group 2 was produced by the addition of bioactive glass with a linear log particle size distribution in a 50/50 ratio by volume. Volumes of bioactive glass compared to sheep bone were determined in the knowledge of mass and density at one standard impaction. Samples from the above four groups were then sent to microbiology for culture to ensure sterility before use.

Bone Defect Grafting 6 metaphyseal defects per limb in a sheep model (12 sheep) were grafted using negative control, impacted autograft as a positive control, and the experimental groups prepared as described above with random placement of graft types along the defect sites. The defect sites were lateral proximal femoral metaphysis (distal to greater trochanter), lateral distal femoral metaphysis, and medial proximal tibial metaphysis, on left and right legs. These sites were chosen as they allowed six relatively accessible defects per sheep, in areas of metaphyseal bone at the end of weightbearing long bones. These areas were considered to simulate to local environment as far as blood flow, cell type and boney architecture were concerned in clinical impaction grafting, although the grafts themselves were not subjected to direct load. Grafts placed in defects were allocated on a Latin Square design. Animals were housed together in a 15×20 m barn and allowed to familiarise themselves with surrounding and human contact. Individual pens were used for the postoperative recovery period. Tetracycline labelling was used to distinguish host from graft bone. Evaluation of the grafts following sacrifice of the animals was conducted at 7 and 14 weeks (6 animals on each occasion) using histomorphometry. Half of each defect was embedded in paraffin and stained to evaluate angiogenesis, and the other half embedded in plastic and cut for histomorphometry.

A Proctors impactor similar to that described in Example 1, but which produced a 15 mm pellet, was manufactured. 15 mm was considered to be the largest defect which could be produced safely in a sheep femur.

Operative Technique

A 15 mm diameter hole was drilled to a depth of 15 mm in cancellous bone at each of the sites. Where required, a 3 mm pilot hole was drilled first, so that positioning in cancellous bone could be confirmed. Bone shavings from the hole were collected for the autograft pellet. A Teflon guide was then aligned over the hole and held in position with two AO Small Fragment screws drilled and tapped appropriately. The is hole was then ready to receive its pellet. The pellet was produced by adding the material in three equal portions, impacting 24 times and rotating the piston upon the addition of each of the three portions.

The small impactor with its piston was then taken over to the operative field and "docked" onto the Teflon guide. The guide is durable, sterilizable and flexible to take in the contours of the underlying bone, preventing any slippage as the pellet is introduced. The piston was then tapped in for 16 mm to introduce the pellet into the 15 mm deep hole, allowing 1 mm for the Teflon guide.

After the pellet had been inserted, the Teflon guide was removed together with its screws. Any residual graft was brushed off flush with the cortex and the area washed of debris.

The area was dried with a swab and polymethylmethacrylate bone cement was poured over the area as a sealant. A cross was imprinted in the cement to mark the position of the defect and allow easier localisation at histological sectioning.

Once the cement had cured the soft tissues were closed over the cement plug with 2/0 Vicryl and the skin closed in the standard fashion.

The impaction rate was approximately 1.5 Hz, similar to the clinical scenario and slow enough to allow fluid to escape. This was maintained throughout the study period.

Results

Regeneration of bone will be observed in defects treated with the biocompatible water-soluble glass and bone graft mixture.

EXAMPLE 3

Hip Replacement Experiments

Hip replacement following proximal femoral over-reaming and impaction grafting of both femur and acetabulum was carried out in 15 sheep using left or right hip randomly.

Full mouth mature Merino wethers (castrated adult males) weighing more than 50 kg were purchased from a single breeder to ensure a uniform environment and genetic background.

The ovine femoral diaphysis is devoid of cancellous bone and is extremely greasy. To simulate a revision situation the proximal femur was "over-reamed" until there is just a thin cortical shell. This provides a good model of the similarly poor environment for surgery as the revision cases seen in humans.

Graft was inserted into the femoral canal by syringe and tamped down. When the femoral canal was more than half full, the femoral stem phantom was used to impact the graft with blows from the hammer. The phantom became increasingly difficult to impact further into the graft, with graft fluid being expelled around the mantle. Impaction at this stage was performed more slowly, to allow the fluid to escape and to allow for any elastic deformation of the graft and femur. Correct phantom ante-version and axial alignment (to restore anatomical head position), with a circumferential graft mantle was aimed for. Close inspection of the cortical ring was maintained at this stage to detect any hairline fractures that might develop. The line on the centralisation rod aligned with the marker in the window of the phantom when correctly seated. Impaction was complete when the addition of more graft prevented the phantom from reaching this line despite further impactive effort. In cases of hairline cracks developing, the phantom was withdrawn slightly, a pair of circlage wires was tensioned around the proximal femur and the phantom was re-impacted.

Seven sheep received pure bone allograft, and eight sheep received a 50/50 (by volume) allograft/BWSG mixture. A further sheep was also included in the plain graft group for micromotion analysis, allowing comparison with a clinically loose implant. Test sheep were euthanised after 84 post operative days, with the control sheep for clinically loose implants being euthanised a week early (due to lameness).

Results

The subsidence of the femoral component in the 50/50 mixture was the same as that observed for the plain 100% bone graft, both of which were moderate by today's literature reports.

The micromotion was similar between the two groups and was in the range of what the literature considers representative values for stable implants.

What is claimed is:

1. An admixture of biocompatible water-soluble glass particles comprising 30 to 85 mole % $P_2O_5$, and morsellised bone particles for use in bone repair, wherein the particle size range and particle size distribution of the whole admixture is pre-selected to be capable of forming a well graded aggregate wherein said admixture does not comprise $SiO_2$.

2. The admixture as claimed in claim 1 wherein the diameters of the biocompatible water-soluble glass particles and of the morsellised bone particles are from 0.1 mm to 10.0 mm.

3. The admixture as claimed in claim 2 wherein the diameters of the biocompatible water-soluble glass particles and of the morsellised bone particles are from 0.5 mm to 6.0 mm.

4. The admixture as claimed in claim 1 wherein the size distribution of the particles in the admixture is selected to approximate to the Fuller curve.

5. The admixture as claimed in claim 1 comprising at least 40% by volume of morsellised bone particles.

6. The admixture as claimed in claim 1 wherein the morsellised bone particles are washed prior to use.

7. The admixture as claimed in claim 1 wherein said biocompatible water-soluble glass particles dissolve over a time period compatible with bone repair.

8. The admixture as claimed in claim 7 wherein said water-soluble glass has the composition:

20–35 mole_% $Na_2O$;

18–30 mole_% $CaO$; and

45–60 mole % $P_2O_5$.

9. The admixture as claimed in claim 1 wherein the water-soluble glass comprises an active ingredient to stimulate bone repair which is controllably released upon dissolution of the glass.

10. A composition for use in repair of bone defects, said composition comprising a well graded aggregate of water-soluble glass particles and morsellised bone particles, said water-soluble glass particles comprising 30 to 85 mole % $P_2O_5$ and wherein said well graded aggregate does not comprise $SiO_2$.

11. A composition as claimed in claim 10 wherein the diameter of said water soluble glass particles and morsellised bone particles is from 0.1 mm to 10.0 mm.

12. The composition as claimed in claim 10 comprising at least 25% by volume of water-soluble glass particles.

13. The composition as claimed in claim 12 comprising at least 40% by volume of water-soluble glass particles.

14. The composition as claimed in claim 10 wherein the morsellised bone particles are washed prior to use.

15. The composition as claimed in claim 10 wherein said water soluble glass particles dissolve over a time period compatible with bone repair.

16. The composition as claimed in claim 15 wherein said water-soluble glass particles have the composition:

20–35 mole_% $Na_2O$;

18–30 mole_% $CaO$; and

45–60 mole % $P_2O_5$.

17. The composition as claimed in claim 10 wherein the water-soluble glass particles comprise an active ingredient to promote bone repair which is controllably released by dissolution of the glass.

18. A method of repairing bone defects, said method comprising packing at least part of said defect with an admixture of biocompatible watersoluble glass particles comprising, 30 to 85 mole % $P_2O_5$ and morsellised bone particles, wherein the particle size range and particle size distribution of the whole admixture is pre-selected to be capable of forming a well graded aggregate and wherein said admixture does not comprise $SiO_2$.

19. The method as claimed in claim 18 wherein a prosthesis is located in said bone defect and wherein said admixture is used therearound.

20. The method as claimed in claim 18 wherein said defect is a primary joint arthroplasty.

21. A method of repairing bone defects, said method comprising packing at least part of said defect with a composition comprising a well graded aggregate of water-soluble glass particles and morsellised bone particles, said water-soluble glass particles comprising 30 to 85 mole % $P_2O_5$ and wherein said well graded aggregate does not comprise $SiO_2$.

22. The method as claimed in claim 21 wherein a prosthesis is located in said bone defect and wherein said composition is used therearound.

23. The method as claimed in claim 21 wherein said defect is a primary joint arthroplasty.

* * * * *